US006363744B2

(12) United States Patent
Finn et al.

(10) Patent No.: US 6,363,744 B2
(45) Date of Patent: Apr. 2, 2002

(54) HYDROCARBON SEPARATION PROCESS AND APPARATUS

(75) Inventors: Adrian Joseph Finn, Sowerby Bridge; Grant Leigh Johnson, Altrincham, both of (GB)

(73) Assignee: Costain Oil Gas & Process Limited, Manchester (GB)

( * ) Notice: Subject to any disclaimer, the term of this patent is extended or adjusted under 35 U.S.C. 154(b) by 0 days.

(21) Appl. No.: 09/755,200

(22) Filed: Jan. 8, 2001

(30) Foreign Application Priority Data

Jan. 7, 2000 (GB) .............................................. 0000327

(51) Int. Cl.$^7$ ................................................. F25J 3/00
(52) U.S. Cl. .......................................... 62/621; 62/623
(58) Field of Search .................................... 62/621, 623

(56) References Cited

U.S. PATENT DOCUMENTS

| 4,157,904 A | 6/1979 | Campbell et al. ............... 62/27 |
| 4,171,964 A | 10/1979 | Campbell et al. ............... 62/24 |
| 4,687,499 A | 8/1987 | Aghili ............................. 62/24 |
| 4,851,020 A | 7/1989 | Montgomery, IV ............. 62/24 |
| 4,889,545 A | 12/1989 | Campbell et al. ............... 62/24 |
| 5,568,737 A | 10/1996 | Campbell et al. ............. 62/621 |
| 5,890,377 A | * 4/1999 | Foglietta ....................... 62/621 |
| 5,983,664 A | * 11/1999 | Campbell et al. ............. 62/621 |
| 5,992,175 A | * 11/1999 | Yao et al. ...................... 62/621 |

FOREIGN PATENT DOCUMENTS

| GB | 2271628 B | 4/1994 |
| GB | 2309072 A | 7/1997 |
| WO | WO 98/50742 | 11/1998 |

* cited by examiner

*Primary Examiner*—Ronald Capossela
(74) *Attorney, Agent, or Firm*—Sterne, Kessler, Goldstein & Fox P.L.L.C.

(57) ABSTRACT

A process is described for separating the heavier hydrocarbons from a gaseous hydrocarbon feed wherein a first separator is employed to separate partially condensed gaseous feed and wherein the vapour portion undergoes work expansion and is fed to a fractionation column. The liquid portion is subcooled in heat exchange with the overhead vapour from the fractionation column, expanded, evaporated to provide refrigeration at a low temperature level, and fed to the fractionation column. The rewarmed residual vapour is subsequently compressed to a pressure suitable for export, with a portion of the compressed gas being cooled, condensed and recycled back to reflux the top section of the fractionation column.

Also described is a process wherein a first separator is employed to separate partially condensed gaseous feed and wherein the vapour portion undergoes work expansion and is fed to a high pressure wash column. The liquid portion is expanded and fed to the base of the high pressure wash column. Bottoms liquid from the wash column is subcooled in heat exchange with the overhead vapour from a fractionation column, expanded, evaporated to provide refrigeration at a low temperature level, and fed to the fractionation column. Vapour from the high pressure wash column is partially condensed, with the liquid portion used to provide reflux to the high pressure wash column and the fractionation column.

The processes are especially applicable to recovery of ethane and heavier components from natural gas. Overall process power requirements are reduced, recovery of the desired heavy hydrocarbons is increased or both of these effects are realised.

43 Claims, 5 Drawing Sheets

HYDROCARBON SEPARATION PROCESS AND APPARATUS

INTRODUCTION AND BACKGROUND

This invention relates to a process, and the apparatus for effecting such a process, for the cryogenic fractionation of gaseous hydrocarbon feeds to extract and recover the valuable heavier components thereof. The invention is particularly concerned with a process for high recovery of ethane and heavier components from a natural gas feed. The process is not limited to the recovery of paraffinic compounds such as ethane found in natural gas, but also, for example, to olefins such as ethylene often found in gases associated with petroleum refining or petrochemicals manufacture.

Conventional processes to effect very high recovery of ethane and heavier components from natural gas typically utilise a combination of heat exchange, turbo-expansion, phase separation and fractionation steps. The use of turbo-expansion produces work, which can be used to drive a compressor to supplement residual gas compression, and by removing energy from the feed gas produces low temperature.

DESCRIPTION OF PRIOR ART

In such conventional processes feed gas is partially condensed in a heat exchange system, which typically includes rewarming residual vapour and may include other cold streams such as refrigerant from a mechanical refrigeration cycle. Partial condensation results in a liquid stream, enriched in the valuable heavy components being recovered and a vapour stream, which may undergo further partial condensation steps. These partial condensation steps result finally in one or more liquid streams and a high pressure vapour stream. The liquid streams are expanded and fed to a demethaniser column, which removes the majority of the methane and lighter components, to produce a stable liquid stream. The high pressure vapour stream is work expanded giving a two phase stream which is fed to the demethaniser at a point above the expanded liquid streams.

It is conventional for the demethaniser column to be refluxed with a stream colder than the expander exhaust. A number of processes have been proposed, which differ in their selected demethaniser reflux stream. These processes do however share the principle of judiciously using heat exchanger surface area to make good use of the available refrigeration and to thus give lower process temperatures. Losses of the valuable ethane and heavier components in the demethaniser overheads can thus be reduced without decreasing the demethaniser column pressure and therefore without excessive power requirement.

These processes give an improvement over traditional processes, which use the expander exhaust as the top feed to the demethaniser. Increasing recovery of ethane and heavier components in these traditional processes requires a reduction in demethaniser and expander exhaust pressure to reduce temperatures. Very high ethane recovery can therefore result in uneconomically high power requirements in either recompression of the residual vapour to required product pressure, external refrigeration to increase liquids condensation or in feed gas compression which also increases liquids condensation.

It is common for the selected source of demethaniser reflux to be lean in the components being recovered. A particularly effective reflux stream is that derived from the demethaniser overheads, which in a process effecting very high recovery of ethane from natural gas may be nearly pure methane. A conventional overhead condenser, condensing overhead vapour at column pressure, can not usually be utilised due to the absence of process streams at a lower temperature to provide the necessary refrigeration. In the process of U.S. Pat. No. 4,889,545, a portion of the demethaniser overhead vapour is compressed in a standalone compressor, such that it can be condensed in heat exchange with other process streams to reflux the demethaniser.

U.S. Pat. Nos. 4,171,964 and 4,157,904 describe processes in which streams relatively rich in ethane are sent to the top of the demethaniser to act as reflux, and thus do not provide very high recovery of ethane. GB 2,309,072 and WO 98/50742 disclose hydrocarbon gas processing apparatus wherein a recycle stream is used to reflux the demethaniser.

Figure 1:
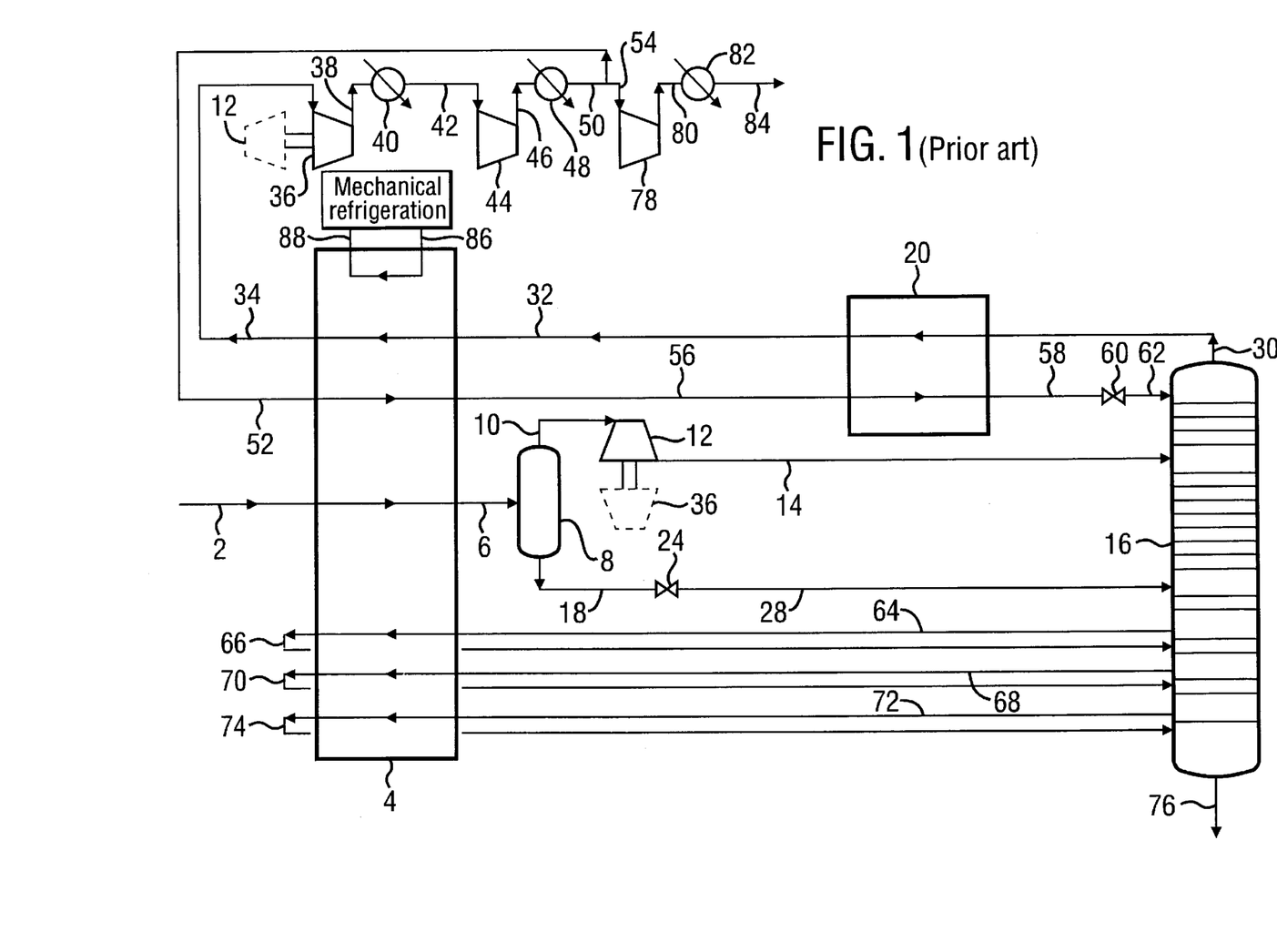
FIG. 1 describes a prior art process for the separation of heavier hydrocarbons from a gaseous hydrocarbon feed.

A configuration in which a portion of the residue gas, which has been rewarmed and compressed to a pressure suitable for export, is recycled, condensed, subcooled and expanded to reflux the demethaniser column shown in FIG. 1. This configuration is less thermodynamically efficient than that of a standalone compressor, due to the losses inherent in warming and re-cooling the residue vapour. The process is however simpler as a standalone compressor is not required.

The pressure at which the recycle stream is cooled and condensed will typically be optimised to minimise residual gas compression power requirement. It is desirable to subcool the recycle stream to within a small approach to the demethaniser overhead temperature, which is the coldest stream in the process. This minimises evolution of vapour on expanding the liquid to column pressure and therefore maximises the liquid available to reflux the rising vapour in the column. At lower recycle stream pressures, compression power requirements are reduced, but the cooling curve becomes less linear and a pinch can occur which limits the temperature to which the recycle stream can be cooled.

SUMMARY OF INVENTION

According to one aspect of the invention there is provided a process for the separation of a heavier hydrocarbon fraction from a gaseous feed comprising a mixture of hydrocarbons, which process comprises:
  (a) cooling the gaseous feed to produce a partially condensed stream
  (b) separating the partially condensed stream to form a first liquid stream and a first gaseous stream
  (c) subcooling at least a portion of the first liquid stream
  (d) expanding said subcooled stream
  (e) passing at least a portion of the expanded stream from (d) as a liquid feed to a fractionation column
  (f) producing a cooled stream by cooling a separated lights fraction of the feed
  (g) recovering said heavier hydrocarbon fraction as a bottoms fraction from said column
characterised in that (i) at least a part of the subcooling required in subcooling step (c) is provided by transfer of heat to the expanded stream from (d), (ii) at least a portion of the cold required to cool the separated lights fraction to produce said cooled stream (f) is provided by transfer of heat to the expanded stream from (d), and (iii) at least a portion of said cooled stream (f) is introduced to an upper part of the column.

It will be appreciated that as a result of having been expanded in step (d) and subjected to a heat transfer operation to provide at least part of the subcooling required from step (c), the feed to the fractionation column will be in an at least partially evaporated state.

In a preferred manner of operation according to the invention at least a part of the subcooling required in subcooling step (c) is provided by transfer of heat to overhead vapour from said fractionation column. When operated in this manner overhead vapour from the fractionation column may be heated in heat exchange with the first liquid stream from step (b) prior to expansion. More preferably a process is provided wherein overhead vapour from the fractionation column and the expanded stream from step (d) are heated in heat exchange with said first liquid stream from step (b) prior to expansion in a single heat exchanger.

It will be appreciated that in accordance with the invention, net refrigeration available within the heat exchanger may be used to cool said stream (f). Preferably the cooled stream (f) comprises a recycle stream derived from overheads from the fractionation column, and is used to reflux the top section of the fractionation column.

By heat-exchanging the first liquid stream and the separated lights fraction with the expanded stream from (d), against the evaporating stream derived from the subcooled stream, a stream of lower temperature is produced that ultimately leads to reduced overheads temperature and increased recovery.

DESCRIPTION OF DRAWINGS

Embodiments of the invention will now be described in more detail with particular reference to the accompanying drawings of which.

In a first embodiment of the invention a process is provided wherein overhead vapour from the fractionation column is rewarmed, compressed and cooled to provide a recycle stream and a residue gas product. Preferably the overhead vapour from the fractionation column and the expanded stream from step (d) are heated in heat exchange with the subcooled first liquid stream from step (b) prior to expansion in a single heat exchanger. This enables small temperature differences to be achieved between cooling and warming streams and gives improved use of available refrigeration.

Figure 2:
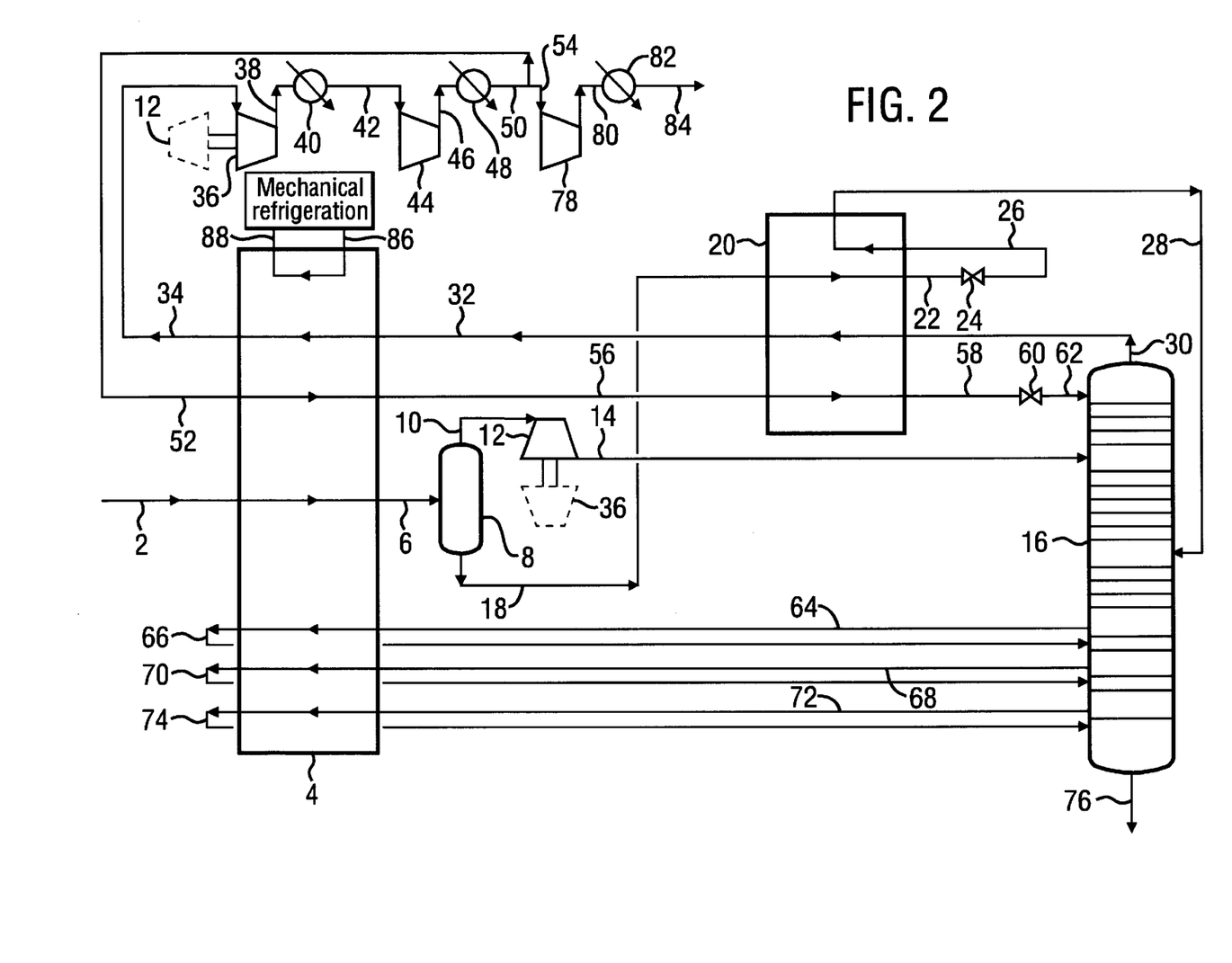
FIG. 2 describes a first embodiment of the present invention wherein a heavier hydrocarbon fraction may be separated from a gaseous hydrocarbon feed. The feed is partially condensed and then separated into the first gaseous stream and the first liquid stream. The first liquid stream is then subcooled in the heat exchanger, expanded, at least partially evaporated, and then passed to the fractionation column.

The process of the present invention according to this embodiment, as shown in FIG. 2, offers an improvement over the conventional residue gas recycle process, by enabling subcooling of the recycle stream to a close approach to the demethaniser overheads temperature at lower recycle pressures than is conventionally possible. Alternatively for a fixed recycle pressure, the recycle stream can be subcooled to a lower temperature. This can result in reduced process power requirement, increased recovery of the desired heavy hydrocarbons or a realisation of both of these effects.

A particular advantage of the process of the invention according to this embodiment is that liquid from the first separator may be subcooled and expanded, providing refrigeration at a temperature level such that it can contribute to the condensation/subcooling of the recycle stream and subcooling of liquid from the first separator. This makes improved use of available refrigeration to remove the restrictive temperature 'pinch' such that the recycle stream can be subcooled to a smaller temperature approach to the demethaniser residue gas. This enables high recovery of the desirable components to be achieved with lower recycle pressures and lower compression power requirements.

Thus in a preferred aspect, this embodiment may also include process elements whereby net refrigeration available with in the heat exchanger is used to cool a further process stream comprising a separated lights fraction of the feed. Preferably this further process stream comprises a recycle stream derived from overheads from the fractionation column. More preferably at least a portion of this recycle stream is condensed/subcooled and returned to an upper part of the fractionation column.

The liquid from the first separator having been subcooled, expanded and evaporated may be fed to the demethaniser column at a mid-stage, as a two phase stream. The location of the feed point may be optimised to maximise process efficiency. In addition to the subcooling, expanding and evaporation of liquid from the first separator, the conventional residual gas recycle process can be further improved by the addition of other process features. These features give improved demethaniser rectification, and for a given recovery of ethane, the required recycle flow of residue gas to reflux the demethaniser is reduced and therefore overall power requirement is reduced.

In one variation of this first embodiment a process is provided wherein the first liquid stream is expanded and separated to give a further gaseous stream and at least a portion of the remainder is subjected the processes of steps (c) and (d).

Figure 3:
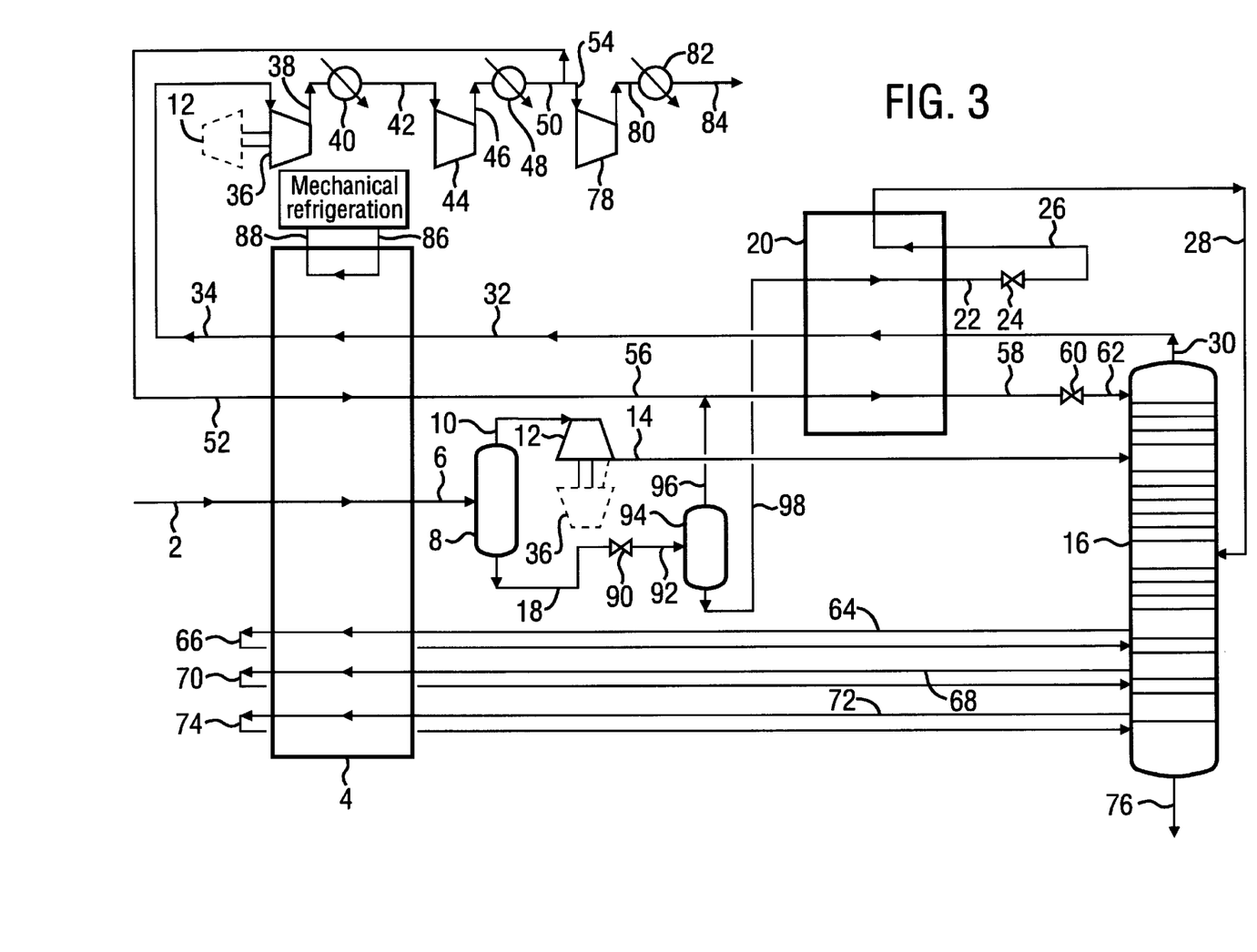
FIG. 3 displays a variation of the first embodiment wherein the first liquid stream is separated into a further liquid stream and a further gaseous stream, and the further liquid stream is then transferred to the fractionation column via the heat exchanger, as in FIG. 2.

This feature of expanding the liquid from the first separator to an intermediate pressure to flash off the lighter components is shown in FIG. 3. The methane rich flash vapour may be separated from the liquid, which may subsequently be subcooled, expanded and evaporated. The flash vapour may be combined with the residual gas recycle stream. For a given reflux flow, the recycle flow is reduced thereby reducing compression power.

Thus the invention also provides a process wherein at least a part of the further gaseous stream is transferred to the fractionation column. Preferably this further gaseous stream or a portion thereof is introduced into the fractionation column at a point above the liquid feed. More preferably the further gaseous stream or a portion thereof is cooled, and optionally expanded prior to its introduction into the fractionation column.

As described above, it is further within the scope of the invention to provide a process wherein the further gaseous stream or a portion thereof is combined with the recycle stream prior to being transferred to the fractionation column. Preferably the further gaseous stream or a portion thereof and the recycle stream are cooled and expanded to produce an at least partially condensed (e.g. liquid) stream which is introduced into the fractionation column. Most preferably the first gaseous stream or a portion thereof and the recycle stream are introduced into the fractionation column at a point above the liquid feed.

In another variation of this first embodiment a process is provided wherein the first gaseous stream is work expanded and separated to give a further gaseous stream and a further liquid stream, said further gaseous stream is partially condensed in a heat exchanger and then fed to the fractionation column. It is preferred that in the process the further gaseous stream is introduced into the fractionation column at a point above the liquid feed. Preferably the further liquid stream is also introduced into the fractionation column.

It is also within the scope of this variation to provide a process wherein the further gaseous stream is partially condensed in heat exchange with the expanded stream from step (d). Preferably overhead vapour from the fractionation column and the expanded stream from step (d) are heated in heat exchange with the first liquid stream from step (b) prior to expansion.

The process of the invention may also be operated in a manner wherein one of said first gaseous stream and said first liquid stream is expanded and separated to give a further gaseous stream and a further liquid stream, or wherein both of said first gaseous stream and said first liquid stream are expanded, combined and separated to give a further gaseous stream and a further liquid stream.

In a preferred aspect a process is provided wherein the first gaseous stream may be work expanded prior to separation.

Figure 4:
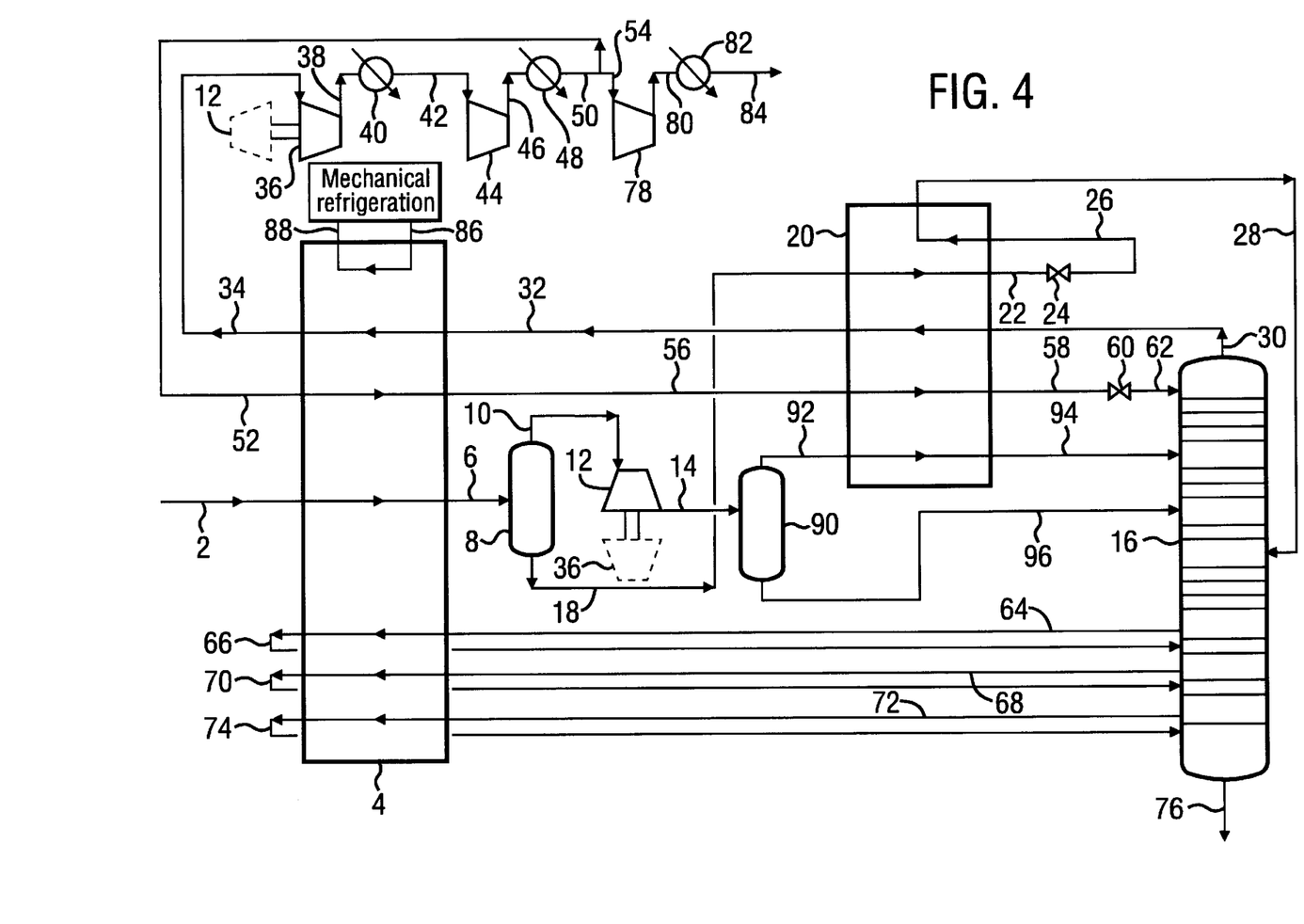
FIG. 4 displays another variation of the first embodiment wherein the first gaseous stream is separated into a further gaseous stream and a further liquid stream, and then both streams are transferred to the fractionation column.

The particular feature described above of separating the two phases of the expander exhaust stream, and subsequently partially condensing the vapour phase in heat exchange with other process streams is shown in FIG. 4. The partially condensed vapour phase may be fed to the column at a separate point above that at which the liquid phase is fed.

Contacting the vapour phase of a partially condensed feed gas with a light hydrocarbon stream can selectively remove the heavier components from that vapour. A process utilising a wash column operating at high pressure to separate the heavier components from a gaseous hydrocarbon feed is described in our copending UK patent application no. 9826999.6. This procedure may be incorporated in the process of the present invention whereby a residual vapour is produced at high pressure from the wash column. Liquid from the wash column is passed to a low pressure fractionation column which produces a stabilised liquid product and a lower pressure residual vapour stream.

In the application of high propane recovery from natural gas, vapour from the top tray of a deethaniser column can be partially condensed to provide reflux to both the deethaniser and the high-pressure wash column. Whilst sufficient reflux can be generated for high recovery of propane and heavier components from natural gas, in most cases, sufficient reflux cannot be generated economically by this route to effect high recovery of ethane and heavier components. For economical high ethane recovery from natural gas, an alternative reflux stream for the high-pressure wash column must therefore be found.

Figure 5:
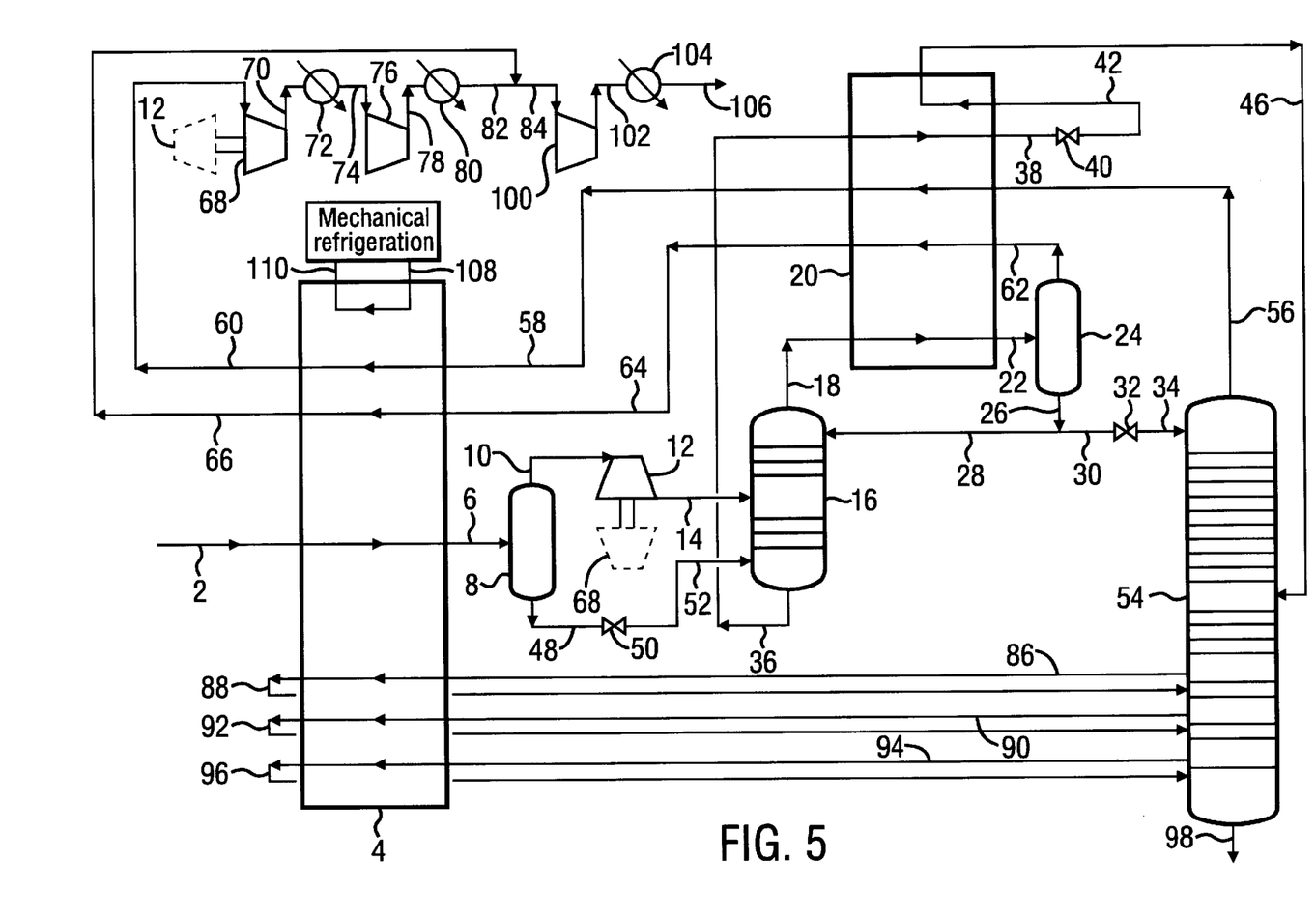
FIG. 5 describes a second embodiment of the invention for separating a heavier hydrocarbon from a gaseous hydrocarbon feed wherein the first liquid stream and the first gaseous stream are transferred to a reequilibration device which produces a first output and a second output. The first output, which is richer in heavier hydrocarbons, is then transferred to the fractionation column via the heat exchanger as in FIG. 2.

In a second embodiment of the invention, the process of subcooling, expanding and evaporating liquid to provide refrigeration at a low temperature level can be applied to a flowsheet using a two column process such that it is suitable for high recovery of ethane and heavier components, as shown in FIG. 5.

In general terms, in the process of this invention according to this embodiment, high pressure vapour from the first separator undergoes work expansion to a medium pressure and is fed to a mid-stage of a wash column. The liquid from the first separator may be expanded to medium pressure and fed to the bottom of the wash column.

The wash column overheads, at a medium pressure, may be partially condensed in a well integrated heat exchange operation. A portion of the liquid may be used to reflux the wash column and the remaining portion expanded and used to reflux the demethaniser. Liquid from the bottom of the wash column may then be subcooled, expanded and rewarmed prior to being fed to the demethaniser column. By this arrangement refrigeration is provided at a temperature level such that it can contribute to the partial condensation of the wash column overheads.

Thus in the second embodiment of this invention there is provided a process wherein the first gaseous stream and the first liquid stream are fed to a reequilibration device which produces a first output, richer in heavier hydrocarbons than the first liquid stream, and a second output, leaner in heavier hydrocarbons than the first gaseous stream, wherein the second output is cooled and partially condensed and directly or indirectly fed to an upper part of the fractionation column as said cooled stream (f) and wherein the first output (which comprises at least a portion of the first liquid stream from step (b)) is subjected to the processes of steps (c) and (d). The reequilibration device may preferably be a high pressure wash column.

In a preferred manner of operation the first gaseous stream is work expanded before being fed to the reequilibration device.

It is within the scope of this embodiment to provide a process wherein the second output is partially condensed in heat exchange with the expanded stream from step (d). Preferably the second output is partially condensed and at least a portion of the first liquid stream from step (b) is subcooled in heat exchange with both the overhead vapour from the fractionation column and the expanded stream from step (d).

The invention also provides a process according to this second embodiment wherein the partially condensed second output is fed to a separator, which produces an additional gaseous stream and an additional liquid stream, wherein at least a portion of the additional liquid stream is fed to an upper part of the fractionation column. Preferably at least a portion of said additional liquid stream is also fed to the reequilibration device.

In a further aspect of this embodiment, the additional gaseous stream may be warmed to produce a residual gas product. Preferably the additional gaseous stream is warmed in heat exchange with at least a portion of the first liquid stream from step (b) prior to expansion. More preferably the additional gaseous stream and the overhead vapour from the fractionation column are warmed in heat exchange with the first liquid stream from step (b) prior to expansion, and the second output from the reequilibration device.

In both embodiments described above, an overhead fraction from the fractionation column may be warmed, and successively compressed and cooled to produce a residue gas product. In the first embodiment of the invention, a portion of this residue gas product is recycled back to reflux the top section of the fractionation column.

The invention further provides apparatus for the separation of a heavier hydrocarbon fraction from a gaseous feed comprising a mixture of hydrocarbons, wherein the mixture is cooled, partially condensed, separated into a first liquid stream and a first gaseous stream and at least a portion of each of the first liquid stream and the first gaseous stream are passed to a fractionation column in which said separation is carried out, which apparatus comprises:

(i) conduit means for transferring at least a portion of the first liquid stream to a heat exchanger in which said portion is subcooled, (ii) means for expanding said subcooled stream, (iii) conduit means for transferring at least a portion of said expanded stream to the heat exchanger in which the subcooling is effected, whereby at least a part of the subcooling is provided by transfer of heat to the expanded stream.

(iv) conduit means for introducing a cooled stream produced by cooling a separated lights fraction of the feed to an upper part of the column, at least a portion of the cold required to cool the separated lights fraction being provided by transfer of heat to said expanded stream The invention further provides apparatus as described above wherein the cooled, partially condensed mixture is separated into a first gaseous stream and a first liquid stream in a first separator, and said apparatus further comprises means for expanding the first liquid stream and means for separating the first expanded liquid stream into a further gaseous stream and a further liquid stream, wherein the further liquid stream is transferred to the heat exchanger.

The above-defined apparatus may further comprise means (e.g. an expansion turbine) for partially condensing the first gaseous stream, separation means for separating at least a portion of the partially condensed stream into a further gaseous stream and a further liquid stream, and means for transferring at least a portion of the further gaseous stream to the fractionation column.

The apparatus of the invention may be adapted for carrying out the second process embodiment of the invention, wherein the cooled, partially condensed mixture is separated into a first gaseous stream and a first liquid stream in a first separator. In this case the apparatus additionally includes (a) means for work expanding said first gaseous stream, (b) means for expanding said first liquid stream, (c) a reequilibration device which is arranged to receive said expanded first gaseous stream and said expanded first liquid stream, and produces a first output which is richer in heavier hydrocarbons than said first expanded liquid stream, and a second output which is leaner in heavier hydrocarbons than said first gaseous stream, (d) conduit means for transferring at least a portion of said second output to the fractionation column, and (e) conduit means for transferring said first output to the heat exchanger.

DESCRIPTION OF SPECIFIC EMBODIMENTS

Embodiment 1

The invention is described below in terms of a process for high ethane recovery. The description should be read in conjunction with the flow diagram in FIG. 2.

A feed gas at an elevated pressure 2 is passed through heat exchange system 4 where it is cooled and partially condensed. The liquid phase 18 is separated from the uncondensed vapour phase 10 in vapour/liquid separator 8. A first gaseous stream comprising vapour 10 is work expanded in turbo-expander 12 to give a two phase stream 14 which is fed to the upper portion of a fractionation column in the form of demethaniser 16. A first liquid stream comprising liquid 18 is cooled in heat exchange system 20 to give sub-cooled liquid 22 which is expanded across valve 24 to give a stream 26 which may be liquid or two phase. Stream 26 is partially evaporated in heat exchange system 20 to give a two phase stream 28 which is fed to a mid-stage of the demethaniser 16.

Refrigeration for feed gas cooling is supplemented by evaporating liquid refrigerant stream 86 in heat exchange system 4 giving refrigerant vapour stream 88. Use of refrigerant from such a mechanical refrigeration cycle is dependent on feed gas composition, required recovery levels and economic factors, and is not an essential feature of the invention.

The residual vapour from the demethaniser 16 is rewarmed and compressed in the following manner. Vapour 30 from demethaniser 16 is warmed in heat exchange system 20 giving gas 32 which is further warmed in heat exchange system 4 to give gas 34. Gas 34 from heat exchange system 4 is compressed in expander brake 36 giving gas 38 which is cooled in cooler 40 giving gas 42. Gas 42 is compressed in 1st stage compressor 44 giving gas 46 which is subsequently cooled in cooler 48 giving gas 50. Gas 52, which is a portion of gas 50 is removed from the compression train, leaving Gas 54. Gas 54 is compressed in 2nd stage compressor 78 to give gas 80 which is cooled in cooler 82 to give a residue gas product 84.

Reflux to the demethaniser is provided in the following manner. Gas 52 from the 1st stage compressor 44 discharge is cooled in heat exchange system 4 giving gas 56 and is condensed and subcooled in heat exchange system 20 giving a subcooled liquid 58. Subcooled liquid 58 is expanded across valve 60 to the demethaniser pressure, giving a two phase stream 62 which is fed to the top of the demethaniser 16.

Demethaniser reboil is provided in the following manner. Liquid 64 is drawn from a tray part way up the demethaniser and thermosyphoned through heat exchange system 4 where it is partially vaporised to give a two phase stream 66 which is fed back to the demethaniser. Similarly, liquid 68 is drawn from a tray lower down the demethaniser than that from which liquid 64 is drawn, and is thermosyphoned through heat exchange system 4 where it is partially vaporised to give a two phase stream 70 which is fed back to the demethaniser. Additionally, liquid 72 is thermosyphoned from the bottom tray and is fed to heat exchange system 4 where it is partially vaporised to give a two phase stream 74 which is fed back to the demethaniser. A stabilised liquid product 76 is drawn from the bottom of the demethaniser.

Operation of the separation apparatus depicted in FIG. 2 is further illustrated by the data in Table 1.

TABLE 1

Material Balance - to be read in conjunction with FIG. 2

| | | Stream | | | | | | | | | |
|---|---|---|---|---|---|---|---|---|---|---|---|
| | | 2 | 10 | 14 | | 22 | 26 | 28 | | 30 | 34 |
| | | | | | Description | | | | | | |
| | | Feed Gas | Expander Inlet | Expander exhaust feed to demethanises | | Subcooled liquid | Expanded liquid | Demethanises lower feed | | Demethanises overheads | LP Residue gas |
| Vapour Fraction | (molar) | 1.0000 | 1.0000 | 0.8551 | 0.8551 | 0.1449 | 0.0000 | 0.0000 | 0.4679 | 0.4679 | 0.5321 | 1.0000 | 1.0000 |
| Temperature | (° C.) | 30.0 | −41.1 | −82.4 | −82.4 | −82.4 | −90.1 | −89.0 | −67.8 | −67.8 | −67.8 | −99.8 | 15.3 |

TABLE 1-continued

| | | | | | | | | | | | | | |
|---|---|---|---|---|---|---|---|---|---|---|---|---|---|
| Pressure | (kPa(a)) | 6996 | 6955 | 2480 | 2480 | 2480 | 6934 | 2501 | 2480 | 2480 | 2480 | 2466 | 2425 |
| Mass Flow | (kg/h) | 296046 | 203372 | 203372 | 162015 | 41357 | 92674 | 92674 | 92674 | 28448 | 64226 | 272281 | 272281 |
| Molar Flow | | | | | | | | | | | | | |
| Nitrogen | (kgmole/h) | 91 | 83 | 83 | 81 | 2 | 9 | 9 | 9 | 8 | 1 | 122 | 122 |
| Methane | (kgmole/h) | 12495 | 10205 | 10205 | 9287 | 918 | 2291 | 2291 | 2291 | 1574 | 717 | 16588 | 16588 |
| Ethane | (kgmole/h) | 1372 | 790 | 790 | 326 | 464 | 582 | 582 | 582 | 83 | 499 | 92 | 92 |
| Propane | (kgmole/h) | 610 | 223 | 223 | 20 | 202 | 387 | 387 | 387 | 10 | 377 | 0 | 0 |
| i-Butane | (kgmole/h) | 76 | 18 | 18 | 0 | 18 | 58 | 58 | 58 | 0 | 57 | 0 | 0 |
| n-Butane | (kgmole/h) | 152 | 30 | 30 | 0 | 30 | 122 | 122 | 122 | 0 | 122 | 0 | 0 |
| i-Pentane | (kgmole/h) | 46 | 6 | 6 | 0 | 6 | 40 | 40 | 40 | 0 | 40 | 0 | 0 |
| n-Pentane | (kgmole/h) | 46 | 5 | 5 | 0 | 5 | 41 | 41 | 41 | 0 | 41 | 0 | 0 |
| n-Hexane | (kgmole/h) | 30 | 2 | 2 | 0 | 2 | 29 | 29 | 29 | 0 | 29 | 0 | 0 |
| n-Heptane | (kgmole/h) | 15 | 0 | 0 | 0 | 0 | 15 | 15 | 15 | 0 | 15 | 0 | 0 |
| n-Octane | (kgmole/h) | 7 | 0 | 0 | 0 | 0 | 7 | 7 | 7 | 0 | 7 | 0 | 0 |
| Total: | (kgmole/h) | 14942 | 11362 | 11362 | 9715 | 1646 | 3581 | 3581 | 3581 | 1675 | 1905 | 16801 | 16801 |

| | | Stream | | | | | | |
|---|---|---|---|---|---|---|---|---|
| | | 52 | 58 | 62 | | 84 | 76 | 86 | 88 |
| | | | | Description | | | | |
| | | Recycle gas | Subcooled recycle | Demethanises reflex | | Residue gas | Liquid product | Refrigerant in | Refrigerant out |
| Vapour Fraction | (molar) | 1.0000 | 0.0000 | 0.0683 | 0.0683 | 0.9317 | 1.0000 | 0.0000 | 0.0000 | 1.0000 |
| Temperature | (° C.) | 30.0 | −96.8 | −102.2 | −102.2 | −102.2 | 30.0 | 24.3 | −40.0 | −40.0 |
| Pressure | (kPa(a)) | 4652 | 4610 | 2480 | 2480 | 2480 | 6996 | 2480 | 111 | 111 |
| Mass Flow | (kg/h) | 67560 | 67565 | 67565 | 4639 | 62926 | 204721 | 91330 | 20903 | 20903 |
| Molar Flow | | | | | | | | | | |
| Nitrogen | (kgmole/h) | 30 | 30 | 30 | 6 | 24 | 91 | 0 | 0 | 0 |
| Methane | (kgmole/h) | 4116 | 4116 | 4116 | 278 | 3837 | 12472 | 23 | 0 | 0 |
| Ethane | (kgmole/h) | 23 | 23 | 23 | 0 | 23 | 69 | 1304 | 0 | 0 |
| Propane | (kgmole/h) | 0 | 0 | 0 | 0 | 0 | 0 | 610 | 474 | 474 |
| i-Butane | (kgmole/h) | 0 | 0 | 0 | 0 | 0 | 0 | 76 | 0 | 0 |
| n-Butane | (kgmole/h) | 0 | 0 | 0 | 0 | 0 | 0 | 152 | 0 | 0 |
| i-Pentane | (kgmole/h) | 0 | 0 | 0 | 0 | 0 | 0 | 46 | 0 | 0 |
| n-Pentane | (kgmole/h) | 0 | 0 | 0 | 0 | 0 | 0 | 46 | 0 | 0 |
| n-Hexane | (kgmole/h) | 0 | 0 | 0 | 0 | 0 | 0 | 30 | 0 | 0 |
| n-Heptane | (kgmole/h) | 0 | 0 | 0 | 0 | 0 | 0 | 15 | 0 | 0 |
| n-Octane | (kgmole/h) | 0 | 0 | 0 | 0 | 0 | 0 | 7 | 0 | 0 |
| Total: | (kgmole/h) | 4169 | 4169 | 4169 | 285 | 3884 | 12632 | 2310 | 474 | 474 |

Summary
Ethane Recovery 95.0%
Propane Recovery 100.0%
Residual Gas Compressor Power 11925 kW @ 75% efficiency
Expander Power Output 2750 kW @ 83% efficiency
Mechanical Refrigeration Compression Power 1415 kW based on single stage @ 75% efficiency
Total power input = 13340 kW The above process may be varied in a number of ways. For example one or more turbo-expansion steps may be utilized, or one or more steps of partial condensation and phase separation may be employed.

Another alternative to the process described above is to use the turbo-expander 12 to drive other rotating equipment, rather than drive a compressor used to supplement the residual gas compressors 44 and 78.

A further process option is to provide or supplement the refrigeration requirement by warming or evaporating the liquid product 76 from the demethaniser, either at the demethaniser pressure or at an elevated or reduced pressure appropriate to downstream processing.

The required refrigeration may also be provided or supplemented by one or more components of a refrigerant fluid being compressed, condensed/subcooled and expanded to one or more pressures enabling evaporation at one or more temperature levels. One or more liquid streams and a first residual vapour stream may result from heat exchange of the feed gas with this mechanical refrigeration cycle.

Yet another possible process improvement is to combine heat exchange systems 4 and 20, or to change heat exchange system 4 into one or more heat exchanger operations. Feed gas 2 may be split to optimise and improve practicability of heat integration within the aforementioned heat exchanger operations, and subsequently recombined to give stream 6.

Also, integration of the feed gas cooling and the demethaniser of the process can be optimised by utilizing more than two or less than two side exchangers.

The first embodiment described above may be varied as shown in FIG. 3. The first liquid stream comprising liquid 18 from the first separator is expanded to an intermediate pressure and the resultant two phase stream 92 is separated in a second vapour/liquid separator 94. The further liquid stream comprising liquid 98 is subcooled in heat exchanger system 20, expanded and partially evaporated in heat exchanger system 20. The further gaseous stream comprising vapour 96 is combined with the residual gas recycle stream 56 and passed to heat exchanger system 20.

A second variation to the first embodiment is shown in FIG. 4. The two phases of stream 14, the expander exhaust, are separated in a second vapour/liquid separator 90. The further liquid stream comprising liquid 96 is fed to the demethaniser. The further gaseous stream comprising vapour 92 is partially condensed in heat exchange system 20 and subsequently fed at a point in the demethaniser above the liquid feed.

Embodiment 2

The second embodiment of the invention is described below in terms of a process for high ethane recovery. The description should be read in conjunction with the flow diagram in FIG. 5.

A feed gas at an elevated pressure 2 is passed through heat exchange system 4 where it is cooled and partially condensed to give a two phase stream 6. The liquid phase 48 is separated from the uncondensed vapour phase 10 in vapour/liquid separator 8. The first gaseous stream comprising vapour 10 is work expanded in turbo-expander 12 to give a two phase stream 14 which is fed to a mid point of a reequilibration device in the form of high pressure wash column 16. A first liquid stream comprising liquid 48 is expanded to a medium pressure across valve 50 to give a two phase stream 52 which is fed to the bottom of the high pressure wash column 16.

Refrigeration for feed gas cooling is supplemented by evaporating liquid refrigerant stream 108 in heat exchange system 4 giving refrigerant vapour stream 110. Use of refrigerant from such a mechanical refrigeration cycle is dependent on feed gas composition, required recovery levels and economic factors, and is not an essential feature of the invention.

A first output from the high pressure wash column comprising liquid 36 is subcooled in heat exchange system 20 to give subcooled liquid 38. Liquid 38 is expanded across valve 40 to give stream 42, which may be liquid or two phase. Stream 42 is partially evaporated in heat exchange system 20 to give a two phase stream 46 which is fed to a mid stage of the demethaniser 54.

A second output from the high pressure wash column comprising vapour 18 is partially condensed in heat exchanger system 20 to give a two phase stream 22. An additional liquid stream comprising liquid 26 is separated from an uncondensed additional gaseous stream comprising vapour 62 in vapour/liquid separator 24. The liquid 26 is split, with a portion 28 being fed to reflux the high pressure wash column 16. The remaining portion 30 is expanded across valve 32 to give a two phase stream 34 which is fed to an upper part of the demethaniser 54, in order to provide the necessary reflux.

The residual vapour from the demethaniser is rewarmed and compressed in the following manner. Vapour 56 from demethaniser is warmed in heat exchange system 20 giving gas 58 which is further warmed in heat exchange system 4 to give gas 60. Gas 60 from heat exchange system 4 is compressed in the expander brake 68 giving gas 70 which is subsequently cooled in cooler 72 giving gas 74. Gas 74 is compressed in 1st stage compressor 76 to give gas 78 which is cooled in cooler 80 to give gas 82. Gas 82 is mixed with gas 66 to give gas 84. Gas 84 is compressed in 2nd stage compressor 100 to give gas 102 which is cooled in cooler 104 to give a residue gas product 106.

The additional gaseous stream from the vapour/liquid separator 24 comprising residual vapour 62 is warmed in heat exchange system 20 giving gas 64 which is further warmed in heat exchange system 4 to give gas 66. Gas 66 from heat exchange system 4 is mixed with gas 82 to give gas 84.

Demethaniser reboil is provided in the following manner. Liquid 86 is drawn from a tray part way up the demethaniser and thermosyphoned through heat exchange system 4 where it is partially vaporised to give a two phase stream 88 which is fed back to the demethaniser. Similarly, Liquid 90 is drawn from a tray lower down the demethaniser than that from which liquid 86 is drawn, and is thermosyphoned through heat exchange system 4 where it is partially vaporised to give a two phase stream 92 which is fed back to the demethaniser. Additionally, liquid 94 is thermosyphoned from the bottom tray and is fed to heat exchange system 4 where it is partially vaporised to give a two phase stream 96 which is fed back to the demethaniser. A stabilised liquid product 98 is drawn from the bottom of the demethaniser.

Operation of the separation apparatus depicted in FIG. 5 is further illustrated by the data in Table 2.

TABLE 2

Material Balance - to be read in conjunction with FIG. 5

| | | Stream | | | | | | | | |
|---|---|---|---|---|---|---|---|---|---|---|
| | | 2 | 10 | 14 | | | 52 | | | 18 | 62 |
| | | | | Description | | | | | | | |
| | | Feed Gas | Expander Inlet | Expander exhaust feed to HP wash column | | | HP wash column lower feed | | | Wash column vapour | HP Residue vapour |
| Vapour Fraction | (molar) | 1.0000 | 1.0000 | 0.7867 | Vapour | Liquid | 0.4308 | Vapour | Liquid | 1.0000 | 1.0000 |
| Temperature | (° C.) | 30.0 | −51.1 | −78.5 | −78.5 | −78.5 | −73.4 | −73.4 | −73.4 | −86.4 | −89.8 |
| Pressure | (kPa(a)) | 6996 | 6955 | 3549 | 3549 | 3549 | 3549 | 3549 | 3549 | 3528 | 3528 |
| Mass Flow | (kg/h) | 296046 | 128859 | 128859 | 95357 | 33501 | 167187 | 54988 | 112199 | 174123 | 106294 |
| Molar Flow | | | | | | | | | | | |
| Nitrogen | (kgmole/h) | 91 | 61 | 61 | 57 | 3 | 31 | 25 | 5 | 92 | 74 |
| Methane | (kgmole/h) | 12495 | 6637 | 6637 | 5503 | 1134 | 5859 | 3156 | 2702 | 10334 | 6409 |
| Ethane | (kgmole/h) | 1372 | 436 | 436 | 161 | 276 | 936 | 102 | 834 | 191 | 47 |

TABLE 2-continued

| | | | | | | | | | | | |
|---|---|---|---|---|---|---|---|---|---|---|---|
| Propane | (kgmole/h) | 610 | 120 | 120 | 13 | 107 | 490 | 11 | 478 | 0 | 0 |
| i-Butane | (kgmole/h) | 76 | 10 | 10 | 0 | 10 | 66 | 0 | 65 | 0 | 0 |
| n-Butane | (kgmole/h) | 152 | 18 | 18 | 0 | 17 | 135 | 1 | 134 | 0 | 0 |
| i-Pentane | (kgmole/h) | 46 | 4 | 4 | 0 | 4 | 42 | 0 | 42 | 0 | 0 |
| n-Pentane | (kgmole/h) | 46 | 3 | 3 | 0 | 3 | 43 | 0 | 43 | 0 | 0 |
| n-Hexane | (kgmole/h) | 30 | 1 | 1 | 0 | 1 | 29 | 0 | 29 | 0 | 0 |
| n-Heptane | (kgmole/h) | 15 | 0 | 0 | 0 | 0 | 15 | 0 | 15 | 0 | 0 |
| n-Octane | (kgmole/h) | 7 | 0 | 0 | 0 | 0 | 7 | 0 | 7 | 0 | 0 |
| Total: | (kgmole/h) | 14942 | 7290 | 7290 | 5735 | 1555 | 7652 | 3296 | 4355 | 10618 | 6530 |

| | | Stream | | | | |
|---|---|---|---|---|---|---|
| | | 28 | 56 | 34 | 38 | 42 |
| | | | | Description | | |
| | | Wash column reflux | Demethanises overheads | Demethanises column reflux | | Subcooled liquid | Expanded liquid |

| | | | | | | | |
|---|---|---|---|---|---|---|---|
| Vapour Fraction | (molar) | 1.0000 | 1.0000 | 0.3062 | Vapour | Liquid | 0.0000 | 0.0000 |
| Temperature | (° C.) | −89.8 | −109.2 | −109.6 | −109.6 | −109.6 | −100.2 | −99.7 |
| Pressure | (kPa(a)) | 3528 | 1735 | 1756 | 1756 | 1756 | 3528 | 1777 |
| Mass Flow | (kg/h) | 106294 | 98435 | 33058 | 9887 | 23172 | 156695 | 156695 |
| Molar Flow | | | | | | | | |
| Nitrogen | (kgmole/h) | 10 | 18 | 9 | 6 | 3 | 9 | 9 |
| Methane | (kgmole/h) | 2012 | 6063 | 1913 | 602 | 1311 | 4173 | 4173 |
| Ethane | (kgmole/h) | 74 | 22 | 70 | 2 | 68 | 1255 | 1255 |
| Propane | (kgmole/h) | 0 | 0 | 0 | 0 | 0 | 610 | 610 |
| i-Butane | (kgmole/h) | 0 | 0 | 0 | 0 | 0 | 76 | 76 |
| n-Butane | (kgmole/h) | 0 | 0 | 0 | 0 | 0 | 152 | 152 |
| i-Pentane | (kgmole/h) | 0 | 0 | 0 | 0 | 0 | 46 | 46 |
| n-Pentane | (kgmole/h) | 0 | 0 | 0 | 0 | 0 | 46 | 46 |
| n-Hexane | (kgmole/h) | 0 | 0 | 0 | 0 | 0 | 30 | 30 |
| n-Heptane | (kgmole/h) | 0 | 0 | 0 | 0 | 0 | 15 | 15 |
| n-Octane | (kgmole/h) | 0 | 0 | 0 | 0 | 0 | 7 | 7 |
| Total: | (kgmole/h) | 2096 | 6103 | 1992 | 610 | 1382 | 6420 | 6420 |

| | | Stream | | | | | |
|---|---|---|---|---|---|---|---|
| | | 46 | 60 | 66 | 84 | 98 | 100 | 102 |
| | | | | Description | | | | |
| | | Demethansis lower feed | | | Recycle gas | HP Residue gas | Residue gas | Liquid product | Refrigerant in | Refrigerant out |

| | | | | | | | | | |
|---|---|---|---|---|---|---|---|---|---|
| Vapour Fraction | (molar) | 0.4454 | Vapour | Liquid | 1.0000 | 1.0000 | 1.0000 | 0.0000 | 0.0000 | 1.0000 |
| Temperature | (° C.) | −84.4 | −84.4 | −84.4 | 24.1 | 24.1 | 30.0 | 6.8 | −40.0 | −40.0 |
| Pressure | (kPa(a)) | 1756 | 1756 | 1756 | 1694 | 3487 | 6996 | 1756 | 111 | 111 |
| Mass Flow | (kg/h) | 156695 | 47674 | 109021 | 98436 | 106294 | 204730 | 91317 | 26437 | 26437 |
| Molar Flow | | | | | | | | | | |
| Nitrogen | (kgmole/h) | 9 | 8 | 1 | 18 | 74 | 91 | 0 | 0 | 0 |
| Methane | (kgmole/h) | 4173 | 2738 | 1436 | 6063 | 6409 | 12473 | 23 | 0 | 0 |
| Ethane | (kgmole/h) | 1255 | 107 | 1148 | 22 | 47 | 69 | 1303 | 0 | 0 |
| Propane | (kgmole/h) | 610 | 6 | 603 | 0 | 0 | 0 | 610 | 600 | 600 |
| i-Butane | (kgmole/h) | 76 | 0 | 76 | 0 | 0 | 0 | 76 | 0 | 0 |
| n-Butane | (kgmole/h) | 152 | 0 | 152 | 0 | 0 | 0 | 152 | 0 | 0 |
| i-Pentane | (kgmole/h) | 46 | 0 | 46 | 0 | 0 | 0 | 46 | 0 | 0 |
| n-Pentane | (kgmole/h) | 46 | 0 | 46 | 0 | 0 | 0 | 46 | 0 | 0 |
| n-Hexane | (kgmole/h) | 30 | 0 | 30 | 0 | 0 | 0 | 30 | 0 | 0 |
| n-Heptane | (kgmole/h) | 15 | 0 | 15 | 0 | 0 | 0 | 15 | 0 | 0 |
| n-Octane | (kgmole/h) | 7 | 0 | 7 | 0 | 0 | 0 | 7 | 0 | 0 |
| Total: | (kgmole/h) | 6420 | 2860 | 3561 | 6103 | 6530 | 12633 | 2309 | 600 | 600 |

Summary
Ethane Recovery 95.0%
Propane Recovery 100.0%
Residual Gas Compressor Power 11528 kW @ 75% efficiency
Expander Power Output 934 kW @ 83% efficiency
Mechanical Refrigeration Compression Power 1790 kW based on single stage @ 75% efficiency
Total power input = 13318 kW The above process may be varied in a number of ways. For example, one or more turbo-expansion steps may be utilized, or one or more steps of partial condensation and phase separation may be employed.

Another alternative to the process described above is to use the turbo-expander 12 to drive other rotating equipment, rather than drive a compressor used to supplement the residual gas compressors 76 and 100.

A further alternative is for one or both of (a) the portion of the additional liquid stream comprising liquid 26 which is fed to reflux the high pressure wash column and (b) the portion of liquid 26 which is fed to an upper part of the demethaniser 54, may be subcooled in heat exchange system 20 prior to passing to either the high pressure wash column 16 or valve 32 respectively.

Yet another possible process improvement is to combine heat exchange systems 4 and 20, or to change heat exchange system 4 into one or more heat exchanger operations. Feed gas 2 may be split to optimise and improve practicability of heat integration within the aforementioned heat exchanger operations, and subsequently recombined to give stream 6.

A further process option is to provide or supplement the refrigeration requirement by warming or evaporating the liquid product 98 from the demethaniser, either at the demethaniser pressure or at an elevated or reduced pressure appropriate to downstream processing. Alternatively, the refrigeration requirement may be provided or supplemented by expanding the residual vapours from the high pressure wash column.

The required refrigeration may also be provided or supplemented by one or more components of a refrigerant fluid being compressed, condensed/subcooled and expanded to one or more pressures enabling evaporation at one or more temperature levels. One or more liquid streams and a first residual vapour stream may result from heat exchange of the feed gas with this mechanical refrigeration cycle.

Integration of the feed gas cooling and the demethaniser of the process can be further optimised by utilizing more than two or less than two side exchangers.

It may also be advantageous within the above process to reboil the high pressure wash column, for example in heat exchange with a portion of feed gas, to reduce the load on the demethaniser.

As a further improvement, reflux to the high pressure wash column may be provided by totally condensing a portion of the high pressure wash column second output, comprising overhead vapour 18, rather than partially condensing the whole of vapour 18.

Also, the vapour and liquid phases of the expander exhaust stream 14 may be separated in a vapour/liquid separator, with the liquid phase being fed to a mid-stage of the high pressure wash column. The vapour phase may be partially condensed in heat exchange system 20 with the resultant two phase stream being fed at a higher point in the high pressure wash column to provide all or part of the required reflux.

We claim:

1. A process for the separation of a heavier hydrocarbon fraction from a gaseous feed comprising a mixture of hydrocarbons, which process comprises:
   (a) cooling the gaseous feed to produce a partially condensed stream,
   (b) separating the partially condensed stream to form a first liquid stream and a first gaseous stream,
   (c) subcooling at least a portion of the first liquid stream,
   (d) expanding said subcooled stream,
   (e) passing at least a portion of the expanded stream from (d) as a liquid feed to a fractionation column,
   (f) producing a cooled stream by cooling a separated lights fraction of the feed, and
   (g) recovering said heavier hydrocarbon fraction as a bottoms fraction from said column,
characterised in that (i) at least a part of the subcooling required in subcooling step (c) is provided by transfer of heat to the expanded stream from (d), (ii) at least a portion of the cold required to cool the separated lights fraction to produce said cooled stream (f) is provided by transfer of heat to the expanded stream from (d), and (iii) at least a portion of said cooled stream (f) is introduced to an upper part of the column.

2. A process according to claim 1 in which at least a part of the subcooling required in subcooling step (c) is provided by transfer of heat to overhead vapour from said fractionation column.

3. A process according to claim 1 wherein overhead vapour from the fractionation column is heated in heat exchange with the first liquid stream from step (b) prior to expansion.

4. A process according to claim 3 wherein overhead vapour from the fractionation column and the expanded stream from step (d) are heated in heat exchange with the first liquid stream from step (b) prior to expansion in a single heat exchanger.

5. A process according to claim 4 wherein net refrigeration available within the heat exchanger is used to cool said separated lights fraction in step (f).

6. A process according to claim 5 wherein said separated lights fraction comprises a recycle stream derived from overheads from the fractionation column.

7. A process of claims 1 wherein overhead vapour from the fractionation column is rewarmed, compressed and cooled to provide a recycle stream and a residue gas product.

8. A process according to claim 7 wherein overhead vapour from the fractionation column and the expanded stream from step (d) are heated in heat exchange with the subcooled first liquid stream from step (b) prior to expansion in a single heat exchanger.

9. A process according to claim 8 wherein net refrigeration available within the heat exchanger is used to cool said separated lights fraction in step (f).

10. A process according to claim 9 wherein said separated lights fraction comprises a recycle stream derived from overheads from the fractionation column.

11. A process according to claim 10 wherein at least a portion of said recycle stream is condensed/subcooled and returned to an upper part of the fractionation column.

12. A process according to claim 1 wherein said first liquid stream is expanded and separated to give a further gaseous stream and at least a portion of the remainder is subjected to the processes of steps (c) and (d).

13. A process according to claim 12 wherein at least a part of said further gaseous stream is cooled to form at least a portion of cooled stream (f).

14. A process according to claim 13 wherein said further gaseous stream or a portion thereof is combined with a recycled stream derived from column overheads to form said separated lights fraction, which is introduced into the fractionation column at a point above the liquid feed.

15. A process according to claim 13 wherein said cooled stream (f) or a portion thereof is expanded prior to its introduction into the fractionation column.

16. A process according to claims 13 wherein said further gaseous stream or a portion thereof is combined with the whole of said recycle stream prior to being transferred to the fractionation column.

17. A process according to claim 1 wherein said cooled stream (f) or a portion thereof is expanded to produce an at least partially condensed stream which is introduced into the fractionation column.

18. A process according to claim 17 wherein said first gaseous stream or a portion thereof is introduced into the fractionation column at a point above the liquid feed.

19. A process according to claims 1 wherein said first gaseous stream is work expanded and separated to give a further gaseous stream and a further liquid stream, said further gaseous stream is partially condensed in a heat exchanger and then fed to the fractionation column.

20. A process according to claim 19 wherein said further gaseous stream is introduced into the fractionation column at a point above the liquid feed.

21. A process according to claim 19 wherein said further liquid stream is also introduced into the fractionation column.

22. A process according to claim 19 wherein said further gaseous stream is partially condensed in heat exchange with said expanded stream from step (d).

23. A process according to claim 22 wherein overhead vapour from the fractionation column and the expanded stream from step (d) are heated in heat exchange with said first liquid stream from step (b) prior to expansion.

24. A process according to claim 1 wherein one of said first gaseous stream and said first liquid stream is expanded and separated to give a further gaseous stream and a further liquid stream.

25. A process according to claim 1 wherein both of said first gaseous stream and said first liquid stream are expanded, combined and separated to give a further gaseous stream and a further liquid stream.

26. A process according to claim 1 wherein said first gaseous stream is work expanded prior to separation.

27. A process according to claims 1 wherein said first gaseous stream and said first liquid stream are fed to a reequilibration device which produces a first output which is richer in heavier hydrocarbons than the first liquid stream, and a second output which is leaner in heavier hydrocarbons than the first gaseous stream, wherein said second output is cooled and partially condensed and directly or indirectly fed to an upper part of the fractionation column as said cooled stream (f) and wherein said first output is subjected to the processes of steps (c) and (d).

28. A process according to claim 27 wherein said first gaseous stream is work expanded before being fed to the reequilibration device.

29. A process according to claim 27 wherein said reequilibration device is a high pressure wash column.

30. A process according to claim 1 wherein said second output is partially condensed in heat exchange with said expanded stream from step (d).

31. A process according to claim 30 wherein said second output is partially condensed and at least a portion of the first liquid stream from step (b) is subcooled in heat exchange with said overhead vapour from said fractionation column and said expanded and at least partially evaporated subcooled stream from step (d).

32. A process according to claim 30 wherein said partially condensed output is fed to a separator, which produces an additional gaseous stream and an additional liquid stream, wherein at least a portion of said additional liquid stream is fed to an upper part of the fractionation column.

33. A process according to claim 32 wherein at least a portion of said additional liquid stream is fed to the reequilibration device.

34. A process according to claim 32 wherein said additional gaseous stream is warmed to produce a residual gas product.

35. A process according to claim 32 wherein said additional gaseous stream is warmed in heat exchange with at least a portion of said first liquid stream from step (b) prior to expansion.

36. A process according to claim 35 wherein said additional gaseous stream and said overhead vapour from said fractionation column are warmed in heat exchange with at least a portion of said first liquid stream from step (b) prior to expansion, and the second output from the reequilibration device.

37. A process according to claims 27 wherein at least a portion of said first output is subcooled, expanded and at least partially evaporated, and at least a portion of the expanded and at least partially evaporated subcooled stream is used as a liquid feed for the fractionation column.

38. A process according to claim 1 wherein an overhead fraction from said fractionation column is warmed, and successively compressed and cooled to produce a residue gas product.

39. A process according to claim 38 wherein a portion of said residue gas product is cooled and recycled to the top of the fractionation column as said cooled stream (f).

40. Apparatus for the separation of a heavier hydrocarbon fraction from a gaseous feed comprising a mixture of hydrocarbons, wherein said mixture is cooled, partially condensed, separated into a first liquid stream and a first gaseous stream and at least a portion of each of the first liquid stream and the first gaseous stream are passed to a fractionation column in which said separation is carried out, which apparatus comprises:

(i) conduit means for transferring at least a portion of the first liquid stream to a heat exchanger in which said portion is subcooled, (ii) means for expanding said subcooled stream, (iii) conduit means for transferring at least a portion of said expanded stream to the heat exchanger in which the subcooling is effected, whereby at least a part of the subcooling is provided by transfer of heat to the expanded stream, and (iv) conduit means for introducing a cooled stream produced by cooling a separated lights fraction of the feed to an upper part of the column, at least a portion of the cold required to cool the separated lights fraction being provided by transfer of heat to said expanded stream.

41. Apparatus according to claim 40 wherein said cooled, partially condensed mixture is separated into a first gaseous stream and a first liquid stream in a first separator, and said apparatus further comprises means for expanding said first liquid stream and means for separating said first expanded liquid stream into a further gaseous stream and a further liquid stream, wherein said further liquid stream is transferred to the heat exchanger.

42. Apparatus according to claim 40 further comprising means for partially condensing the first gaseous stream, separation means for separating at least a portion of said partially condensed stream into a further gaseous stream and a further liquid stream, and means for transferring at least a portion said further gaseous stream to the fractionation column.

43. Apparatus according to claim 40 wherein said cooled, partially condensed mixture is separated into a first gaseous stream and a first liquid stream in a first separator, and said apparatus includes (a) means for work expanding said first gaseous stream, (b) means for expanding said first liquid stream, (c) a reequilibration device which is arranged to receive said expanded first gaseous stream and said expanded first liquid stream, and produces a first output which is richer in heavier hydrocarbons than said first expanded liquid stream, and a second output which is leaner in heavier hydrocarbons than said first gaseous stream, (d) conduit means for transferring at least a portion of said second output to the fractionation column, and (e) conduit means for transferring said first output to the heat exchanger stream into a further gaseous stream and a further liquid stream, wherein said further liquid stream is transferred to the heat exchanger.

* * * * *